United States Patent
Drab et al.

[19]

[11] Patent Number: 6,125,871
[45] Date of Patent: Oct. 3, 2000

[54] VALVE ASSEMBLY WITH FLUSH AND SAMPLE CAPABILITY

[75] Inventors: Gilbert J. Drab, Irving; Christopher M. Sweeney, Magnolia; Akimoto Ochi, The Woodlands, all of Tex.

[73] Assignee: Ashland, Inc., Covington, Ky.

[21] Appl. No.: 09/235,886

[22] Filed: Jan. 22, 1999

[51] Int. Cl.[7] .............................. G01N 1/10; B08B 3/04
[52] U.S. Cl. ..................... 137/15.05; 73/863.86; 73/864.33; 134/113; 134/115; 134/169 R; 137/240; 137/637.05; 137/614; 141/1; 141/91; 141/346; 141/386; 222/148; 422/68.1; 422/103
[58] Field of Search ................... 73/863.86, 864.33; 134/113, 115, 169 R; 137/15, 614.02, 614.06, 637.05, 240, 15.05, 15.06; 141/89, 90, 91, 346, 382, 383, 386, 387, 388; 222/148; 422/68.1, 83, 103

[56] References Cited

U.S. PATENT DOCUMENTS

| | | | |
|---|---|---|---|
| 2,872,216 | 2/1959 | Kaiser ............................... | 137/637.05 |
| 2,919,144 | 12/1959 | Lindenmeyer ..................... | 137/637.05 |
| 3,528,447 | 9/1970 | Kolb .................................. | 137/614 |
| 4,186,759 | 2/1980 | Stevenson et al. ................. | 141/91 |
| 4,499,932 | 2/1985 | Perigo et al. ...................... | 141/91 |
| 4,566,489 | 1/1986 | Knapp et al. ...................... | 137/614 |
| 4,989,630 | 2/1991 | Yonezawa .......................... | 137/240 |
| 5,058,619 | 10/1991 | Aheng ................................ | 137/240 |
| 5,088,519 | 2/1992 | Giroux et al. ..................... | 137/240 |
| 5,213,309 | 5/1993 | Makishima ........................ | 141/346 |
| 5,311,899 | 5/1994 | Isayama et al. ................... | 137/240 |
| 5,343,907 | 9/1994 | Wagner .............................. | 137/240 |
| 5,348,192 | 9/1994 | Sardynski et al. ................. | 137/240 |
| 5,649,563 | 7/1997 | Shimano ............................ | 137/240 |
| 5,823,222 | 10/1998 | Minshull et al. .................. | 73/863.86 |
| 5,914,092 | 6/1999 | Moon ................................. | 73/863.86 |

*Primary Examiner*—George L. Walton
*Attorney, Agent, or Firm*—Mueller and Smith, LPA

[57] ABSTRACT

A chemical fluid valve transfer (e.g., load/unload) assembly is formed from a male valve assembly and a female valve assembly. The male valve assembly is fitted with a male connector which houses a chamber that is connected to a flush inlet line, and a flush outlet line, and a chemical transport line. The female valve assembly is fitted with a female connector which mates with the male valve assembly male connector for interconnecting the male valve and female valve assemblies, and fitted with a chemical transport line. Another aspect of the present invention is a method for transferring a chemical fluid between a tanker fitted with a female coupler and a fill/unload station fitted with a male coupler and hose assembly. This method involves the connecting of the tanker hose and the fill station hose with the valve assembly described above. Next, the male and female connectors and said chamber are purged with liquid or gaseous cleaning fluid admitted via the flush inlet flush line and withdrawn via the flush outlet line. One of the male valve assembly or the female valve assembly then is opened to permit the chemical fluid to enter into the chamber for withdrawal therefrom via the flush outline line for its sampling. Finally, the chemical fluid is transferred between the tanker and the fill station through the valve assembly.

8 Claims, 2 Drawing Sheets

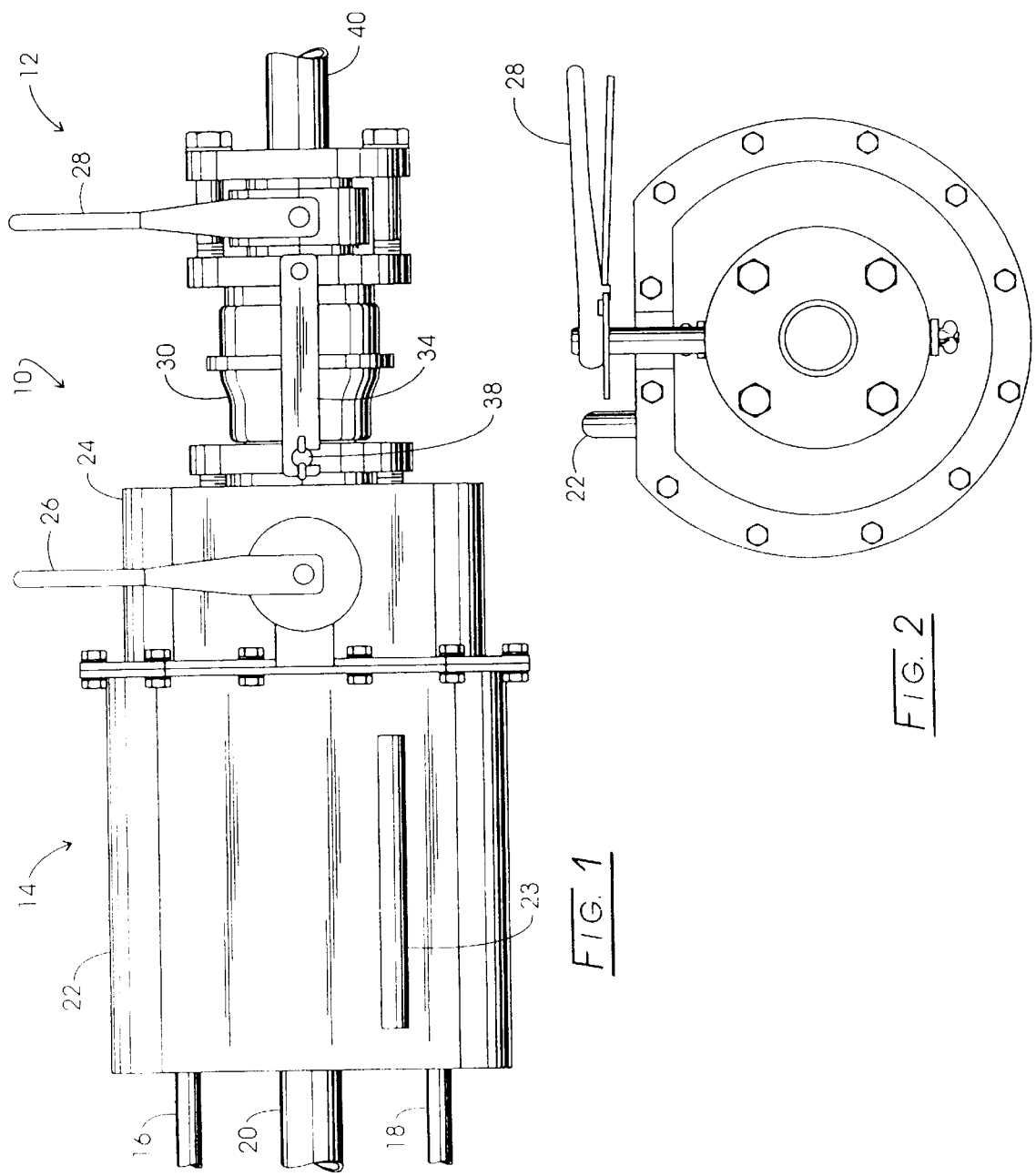

VALVE ASSEMBLY WITH FLUSH AND SAMPLE CAPABILITY

CROSS-REFERENCE TO RELATED APPLICATIONS

None

STATEMENT REGARDING FEDERALLY SPONSORED RESEARCH

Not applicable.

BACKGROUND OF THE INVENTION

The present invention relates generally to the loading and unloading of bulk tankers and more particularly to a valve assembly with flush and sample capability for maintaining chemical purity of the material to be loaded or unloaded.

The need exists in the electronic semiconductor chemical business to load and unload high purity chemicals into bulk road tankers (e.g., 3,000 to 8,000 gallons) and rail tankers (e.g., 10,000 to 20,000 gallons) under conditions that maintain chemical purity and worker safety, while preventing spillage into the environment. Moreover, it would be convenient also to obtain samples for chemical certification prior to the loading/unloading procedure again while preventing spillage into the environment and without contaminating the chemical being loaded/unloaded.

Presently, a sample valve is bolted to 2-inch flange connections and the tanker is pressurized to obtain a sample upstream of the flange connection for certification. The tanker fill valve then is opened to permit loading/unloading. This method will contaminate the chemical being transferred at the point of connection and is a safety issue and environmental concern with operating personnel disconnecting the flanged flex hose assemblies with chemical residue after chemical transfers.

Thus, there exists a need in the art to be able to environmentally safely transfer high purity chemicals while being able to sample with chemical for chemical purity without risking its contamination. Such need is addressed by the present invention.

BRIEF SUMMARY OF THE INVENTION

A chemical fluid valve transfer (e.g., load/unload) assembly is formed from a male valve assembly and a female valve assembly. The male valve assembly is fitted with a male connector which houses a chamber that is connected to a flush inlet line, a flush outlet line, and a chemical transport line. The female valve assembly is fitted with a female connector which mates with the male valve assembly male connector for interconnecting the male valve and female valve assemblies, and fitted with a chemical transport line. When the male valve assembly and the female valve assembly are interconnected, the male and female connectors and the chamber can be cleansed with liquid or gaseous cleaning fluid via the flush inlet with internal spray nozzle and flush outlet lines. Also, the chamber is in fluid communication with the female valve assembly chemical transport line. One of the male valve assembly or the female valve assemblies can be opened to permit chemical fluid to enter into the male and female connectors and the chamber for withdrawal therefrom via said flush outline line for its sampling.

Another aspect of the present invention is a method for transferring a chemical fluid between a tanker fitted with a female coupler and a fill/unload station fitted with a male coupler and hose assembly. This method involves the connecting of the tanker hose and the fill station hose with a valve assembly. This valve assembly includes a male valve assembly fitted with a male connector which houses a chamber, a flush inlet line, and a flush outlet line, and a chemical transport line; and a female valve assembly fitted with a female connector which mates with the male valve assembly male connector for interconnecting the male valve and female valve assemblies, and a chemical transport line. Next, the male and female connectors and said chamber are purged with liquid or gaseous cleaning fluid admitted via the flush inlet flush line and withdrawn via the flush outlet line. One of the male valve assembly or the female valve assembly then is opened to permit the chemical fluid to enter into the chamber for withdrawal therefrom via the flush outline line for its sampling. Finally, the chemical fluid is transferred between the tanker and the fill station through the valve assembly.

BRIEF DESCRIPTION OF THE DRAWINGS

For a fuller understanding of the nature and objects of the present invention, reference should be made to the following detailed description taken in conjunction with the accompanying drawings, in which:

FIG. 1 is a side elevational view of the novel chemical fluid valve load/unload assembly where the male valve assembly and the female valve assembly are interconnected;

FIG. 2 is an end view of the interconnected assemblies of FIG. 1; and

Figure 3:
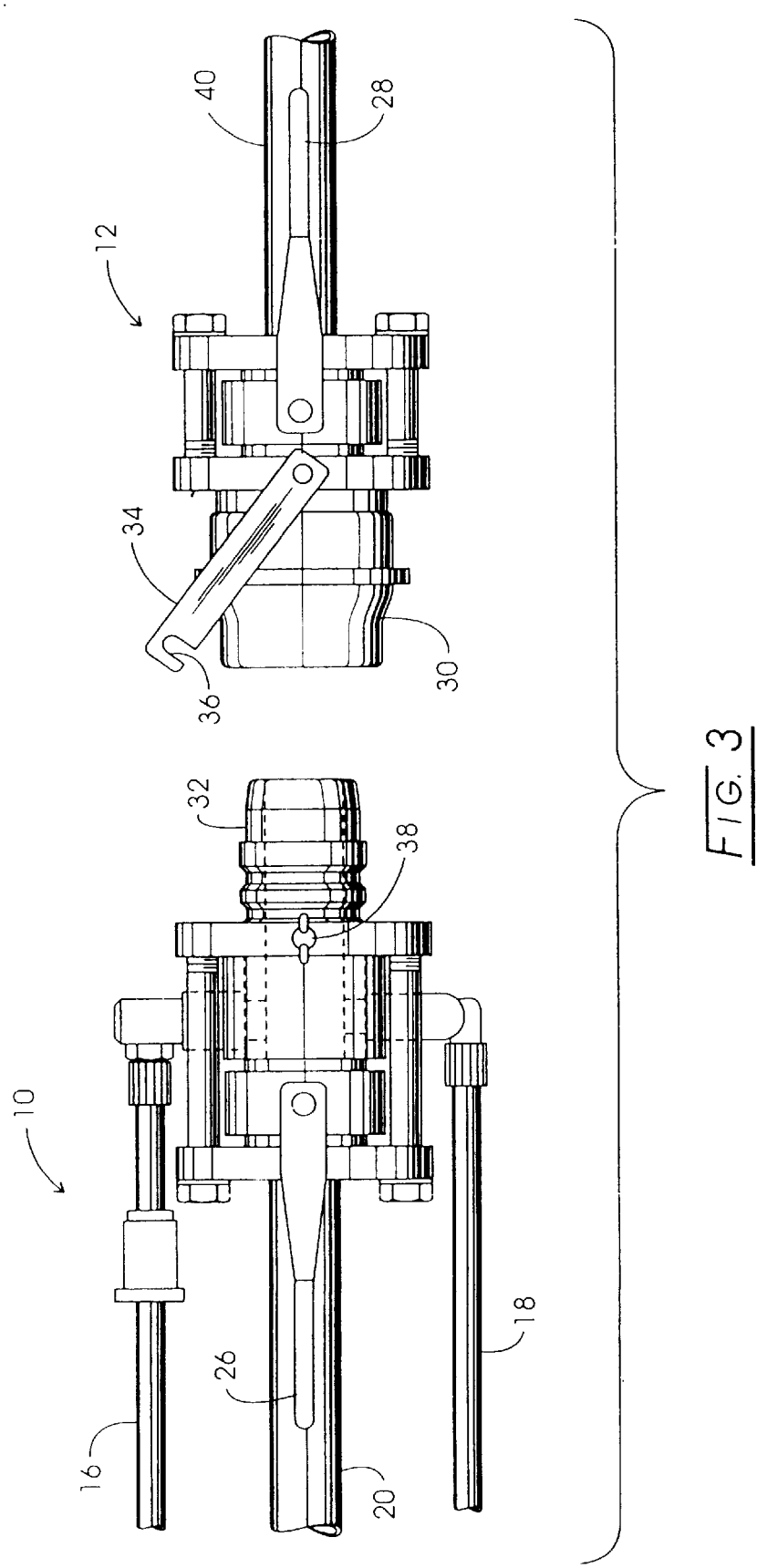
FIG. 3 is a side elevational view of the novel chemical fluid valve load/unload assembly with the male valve assembly and the female valve assembly in unconnected condition.

The drawings will be described in detail below.

DETAILED DESCRIPTION OF THE INVENTION

The inventive chemical fluid valve load/unload assembly is unique in its provision of a sampling chamber that can be cleansed with liquid and/or gaseous cleaning fluids prior to the chemical fluid being sampled for analysis. Moreover, this same sampling chamber can be cleansed following the loading/unloading of the chemical fluid so ensure that no spillage of the chemical fluid to the environment occurs. The operation of such a chemical fluid valve load/unload assembly can be accomplished remotely so as to not expose workers to the chemical fluid during the entire operation. A truly valve assembly with truly unique capabilities, thus, is disclosed herein.

Referring in initially to FIGS. 1 and 2, shown is male valve assembly 10 interconnected to female valve assembly 12. Male valve assembly 10 suitably is connected to the fill station for filling a tanker (e.g., bulk road tankers or rail tank cars) while female valve assembly 12 is connected to the tanker itself. It should be understood, however, that male valve assembly 10 easily could be connected to the tanker and female valve assembly 12 could be connected to the fill station. Such locations of male valve assembly 10 and female valve assembly 12, as described herein, are for illustration of the present invention and is not by way of limitation.

Shroud 14 fits over male valve assembly 10 to protect flush inlet line 16, flush outlet line 18, and chemical transport line 20, as well as shut-off valves provided in lines 16 and 18 (not shown in the "drawings") Handle 23 facilitates installation and removal of shroud 14 from male valve assembly 10. Shroud 14 is composed of flanged sections 22 and 24 that bolt together at their mating flanges. Shroud section 24 has a slot to receive butterfly valve 26.

Female valve assembly 12 houses butterfly valve 28. The bore and encapsulated O-ring assembly (not shown in the "drawings") are disposed within stainless steel housing 30 and mate with male connector 32. Being a "quick connect" and "quick disconnect" system, housing 30 and male connector 32 snap together. Security clamp 34 is pivotally connected at its proximal end to female valve assembly 12 and has slot 36 (see FIG. 3) at its distal end that engages stanchion 38 located on male valve assembly 10. Chemical transport line 40 also can be seen to be in fluid communication with female connector 30 via valve 28. During times of non-use a male plug (like male connector 32) is inserted into housing 30 to protect the housed bore finish and O-ring seal (preferably made from Teflon® brand polytetrafluoroethylene).

Referring now to FIG. 3, shroud 14 has been removed from male valve assembly 10 to reveal the connection lines 16 and 18 to male valve assembly 10. Specifically, chamber 42 within male valve assembly 10 is shown in dashed lines and is seen to be in fluid communication with lines 16 and 18. Chamber 42 also is in fluid communication with line 26 via butterfly valve 26 and line 40 via butterfly valve 34. Such fluid communication is seen to be operative by the handle positions of butterfly valves 26 and 40.

Via flush inlet line 16, liquid and/or gaseous cleaning fluid can be admitted into chamber 42 to wash or cleanse it and then be withdrawn via flush outlet line 18. While a variety of schemes can be envisioned for use with the novel chemical fluid valve load/unload assembly of the present invention, two representative schemes will be described below for purposes of illustrating the present invention.

Tankers being loaded with a chemical fluid are positioned in fill stations that are equipped with male valve assembly 10 which is mated with female valve assembly 12 that is located on the road or rail tanker. Security clamp 34 is engaged about stanchion 38 to prevent accidental separation of assemblies 10 and 12 during transfer of the chemical fluid that are placed under pressure during the loading and unloading operations. Chamber 42 then is flushed with gaseous nitrogen that is admitted via flush inlet line 16 and withdrawn via outlet flush line 18. Suitable shut-off valves are provided in lines 16 and 18 in conventional fashion and their distal ends are connected to sources of fluids admitted via line 16 into chamber 42 and to waste tanks for the fluids withdrawn via line 18.

Chamber 42 next is purged with high purity water and gaseous nitrogen a second time. Finally, chamber 42 is purged with the chemical fluid that is being transferred. Thereafter, butterfly valve assembly 26 is moved to an open position to admit the chemical fluid being loaded and a small sample withdrawn via line 18 and sent to an analytical laboratory for load certification. Following confirmation of the sample, butterfly valve 28 is opened and the tanker loaded with the chemical fluid flowing from line 20 eventually through line 40 for such tanker loading. Thereafter, chamber 42 again is purged with gaseous nitrogen, high purity water, and gaseous nitrogen to ensure complete removal of the chemical fluid therefrom. Male valve assembly 10 then can be disconnected from female valve assembly 12. It should be noted that control of the foregoing operations could be exercised remotely by operation personnel to distance them from the hazardous operations described. Such remote actuation of the purging and loading/unloading operations can be structured by those skilled in such art.

As another example, the foregoing operations can be repeated in order to unload a tanker filled with the chemical fluid. In such case, the tanker would be pressurized (e.g., with inert gas) in order to effect the movement of the chemical fluid from the tanker to the fill station. Also, the chemical fluid would move from line 40 into line 20. Otherwise, the purging and sampling operations would be the same for the unloading operation as described above for the loading operation.

As evident from the foregoing description, materials of construction are suitable for handling pressure and the types of chemical fluids being transferred. Appropriate seals, valves, piping, and other equipment, then, also are provided in conventional fashion.

While the invention has been described and illustrated in connection with certain preferred embodiments thereof, it will be apparent to those skilled in the art that the invention is not limited thereto. Accordingly, it is intended that the appended claims cover all modifications that are within the spirit and scope of this invention. All references cited herein are expressly incorporated herein by reference.

What is claimed is:

1. A chemical fluid valve transfer assembly which comprises:

(a) a male valve assembly having a selectively operable male valve and being fitted with a male connector which houses a chamber that is connected to a flush inlet line and a flush outlet line, and fitted with a chemical transport line that is in fluid communication with said chamber through said male valve; and (b) a female valve assembly having a selectively operable female valve and being fitted with a female connector which mates with said male valve assembly male connector for interconnecting said male valve and female valve assemblies, and fitted with a chemical transport line that is in fluid communication with said chamber through said female valve when said female valve assembly is mated with said male valve assembly;

whereby when said male valve assembly and said female valve assembly are interconnected into a unitary assembly, said male and female connectors and said chamber can be cleansed of contaminants with liquid or gaseous cleaning fluid via said flush inlet with said flush outlet line while said selectively operable male and female valves both are selectively closed, and thereafter one of said male valve assembly or said female valve assembly can be selectively opened and the other valve assembly remain selectively closed to permit chemical fluid to enter into said chamber for withdrawal therefrom via said flush outline line for its sampling to determine chemical purity of said chemical fluid prior to being transferred, wherein said valve assemblies remain interconnected into a unitary assembly during the operations of cleansing, sampling, and transporting.

2. The chemical fluid valve transfer assembly of claim 1, wherein a security clamp is carried by either said male valve assembly or said female valve assembly for clamping said male valve assembly to said female valve assembly.

3. The chemical fluid valve transfer assembly of claim 1, wherein a shroud surrounds said a flush inlet line, and a flush outlet line, and a chemical transport line at their connection to said male valve assembly.

4. The chemical fluid valve transfer assembly of claim 1, wherein said female connector is surrounded by a housing.

5. A method for transferring a chemical fluid between a tanker fitted with a female coupler and a fill/unload station fitted with a male coupler and hose assembly, which comprises the following steps:

(a) connecting said tanker coupler and said fill station hose with a valve assembly which comprises (i) a male valve assembly having a selectively operable male valve and being fitted with a male connector which houses a chamber that is connected to a flush inlet line and a flush outlet line, and fitted with a chemical transport line that is in fluid communication with said chamber through said male valve, interconnected with (ii) a female valve assembly having a selectively operable female valve and being fitted with a female connector which mates with said male valve assembly male connector for interconnecting said male valve and female valve assemblies, and fitted with a chemical transport line that is in fluid communication with said chamber through said female valve when said female valve assembly is mated with said male valve assembly;

(b) purging said male and female connectors and said chamber of contaminants with liquid or gaseous cleaning fluid admitted via said flush inlet flush line and withdrawn via said flush outlet line while said male and female valve assemblies remain interconnected;

(c) after said purging and while said male and female valve assemblies remain interconnected, selectively opening one of said male valve assembly or said female valve assembly with the other valve assembly remaining selectively closed to permit said chemical fluid to enter into said chamber for withdrawal therefrom via said flush outline line for its sampling to determine chemical purity of said chemical fluid prior to being transferred; and (d) transferring said chemical fluid between said tanker and said fill station through said valve assembly while said male and female valve assemblies remain interconnected.

6. The method of claim 5, wherein said cleaning fluid is one or more of high purity water or gaseous nitrogen.

7. The method of claim 5, wherein following said purging with said cleaning fluid, chemical fluid to be transferred is used to purge said male and female connectors and said chamber.

8. The method of claim 5, wherein following said transferring in step (d), said purging step (c) is repeated.

* * * * *